United States Patent
Golmohammadi Ghane et al.

(10) Patent No.: US 11,506,673 B2
(45) Date of Patent: Nov. 22, 2022

(54) MEASUREMENT OF BILIRUBIN CONCENTRATION IN BLOOD SAMPLES

(71) Applicants: Hamed Golmohammadi Ghane, Tehran (IR); Raziyeh Sadat Tabatabaee, Tehran (IR); Seyyed Hamid Ahmadi, Tehran (IR)

(72) Inventors: Hamed Golmohammadi Ghane, Tehran (IR); Raziyeh Sadat Tabatabaee, Tehran (IR); Seyyed Hamid Ahmadi, Tehran (IR)

(*) Notice: Subject to any disclaimer, the term of this patent is extended or adjusted under 35 U.S.C. 154(b) by 423 days.

(21) Appl. No.: 16/686,262

(22) Filed: Nov. 18, 2019

(65) Prior Publication Data
US 2020/0088744 A1 Mar. 19, 2020

Related U.S. Application Data

(60) Provisional application No. 62/768,917, filed on Nov. 18, 2018.

(51) Int. Cl.
*G01N 33/72* (2006.01)
*G01N 21/31* (2006.01)

(52) U.S. Cl.
CPC .......... *G01N 33/728* (2013.01); *G01N 21/31* (2013.01); *G01N 2021/3148* (2013.01)

(58) Field of Classification Search
None
See application file for complete search history.

(56) References Cited

U.S. PATENT DOCUMENTS

2013/0161190 A1* 6/2013 Ewart ............... B01L 3/502
204/403.03

OTHER PUBLICATIONS

Anjana, R. R., J. S. Anjali Devi, M. Jayasree, R. S. Aparna, B. Aswathy, G. L. Praveen, G. M. Lekha, and George Sony. "S, N-doped carbon dots as a fluorescent probe for bilirubin." Microchimica Acta 185, No. 1 (2018): 1-11. (Year: 2018).*
Morales-Narváez, Eden, Hamed Golmohammadi, Tina Naghdi, Hossein Yousefi, Uliana Kostiv, Daniel Horák, Nahid Pourreza, and Arben Merkoçi. "Nanopaper as an optical sensing platform." ACS nano 9, No. 7 (2015): 7296-7305. (Year: 2015).*

* cited by examiner

*Primary Examiner* — Elizabeth A Robinson
*Assistant Examiner* — Ryan J Dowty
(74) *Attorney, Agent, or Firm* — Bajwa IP Law Firm; Haris Zaheer Bajwa

(57) ABSTRACT

A method for measuring bilirubin concentration in a sample includes preparing a sensing element, where the sensing element may include a plurality of carbon dots, adding the sample to the sensing element, where the sample may include a plurality of bilirubin molecules, obtaining a first grayscale image of the sensing element under ultra-violet (UV) irradiation, irradiating visible light with a wavelength between 470 nm and 490 nm on the sensing element, obtaining a second grayscale image of the sensing element under ultra-violet (UV) irradiation, calculating a light intensity difference by calculating a difference between a first average light intensity of the first grayscale image and a second average light intensity of the second image, and determining the bilirubin concentration based on a correlation between the bilirubin concentration and the light intensity difference.

2 Claims, 12 Drawing Sheets

MEASUREMENT OF BILIRUBIN CONCENTRATION IN BLOOD SAMPLES

CROSS-REFERENCE TO RELATED APPLICATION

This application claims the benefit of priority from U.S. Provisional Patent Application Ser. No. 62/768,917, filed on Nov. 18, 2018, and entitled "SMARTPHONE-BASED BILIRUBIN ASSAY KIT," which is incorporated herein by reference in its entirety.

TECHNICAL FIELD

The present disclosure relates to biomolecular diagnostics and particularly relates to bilirubin assay kits. More particularly, the present disclosure is related to a system and method for visual determination of bilirubin levels in a blood sample and applications thereof in diagnosing jaundice.

BACKGROUND

One of the neonatal health concerns for parents is the risk of a newborn baby to have neonatal jaundice. Neonatal jaundice or hyperbilirubinemia is a condition in which the skin gets a yellow tint, and the whites of eyes turn yellow, orange, or brown due to the accumulation of excess (over 2-3 mg dL-1) Bilirubin (BR) in the blood. Nearly 60% of term and 80% of preterm infants have jaundice in the first days of their lives.

BR is a yellowish compound that is produced during the destruction process of aged red blood cells in the liver. The breakdown of heme is followed by the production of biliverdin as the first step of catabolism and BR is created through the reduction of biliverdin with bilirubin reductase enzyme.

There are two types of BR, namely, conjugated BR and unconjugated BR. Conjugated BR is water-soluble and may easily be excreted in urine and feces. Unconjugated BR is a water-insoluble form of BR that may cause neonatal jaundice. The average BR level in infants' blood is about 2 mg $dL^{-1}$ and may be under 5 mg $dL^{-1}$ within the first 12 hours of birth. Many infants, however, have jaundice, and their blood BR level rises above 5 mg $dL^{-1}$ within the first few days after birth. For the first 72 hours of birth, a BR level in the bloodstream of a baby more than 15 mg $dL^{-1}$ increases the risk of hyperbilirubinemia.

Untreated severe jaundice may cause deafness, cerebral palsy, acute bilirubin encephalopathy, and kernicterus in neonates. Due to these serious health concerns, the accurate and timely diagnosis and, consequently, early treatment of jaundice are arguably crucial. Accordingly, there is a need for the development of an accurate diagnostic/analytical method for determining BR levels in blood samples taken from newborn babies to determine whether they have jaundice. Different methods have been developed for the determination of BR levels in biological fluids, including spectroscopic, electrochemical, and liquid chromatographic methods. Although these approaches have demonstrated good performance for BR detection, most of these methods require high volumes of samples, toxic chemicals, and also relatively expensive, large, and sophisticated laboratory equipment. This laboratory equipment in most instances may only be operated by trained operators which consequently may restrict their applications to laboratories.

Moreover, the laboratory turnaround time (TAT) of these approaches from sample collection to obtaining the test results is too long and may lead to a decrease in the real-time estimation possibility for point of care testing (POCT) systems. There are some portable BR meters which are hand-held and operate in transcutaneous settings. These portable and hand-held BR meters may be utilized for POCT and their results are obtained based on the skin color of infants. However, hemoglobin is the primary absorber of visible light in the dermis, especially in the regions 400-425 nm and 500-600 nm and competes with the absorbance of BR and consequently affects the results obtained by these portable and hand-held BR meters. Moreover, transcutaneous bilirubin measurements in newborns do not have the same accuracy as blood-based methods. The results of transcutaneous bilirubin measurements will be different depending on where the sample is taken (e.g., forehead, sternum, and interscapular region). Within the first hours after birth, the transcutaneous bilirubinometers overestimate the TcB by at least 2-3 mg $dL^{-1}$ in comparison to TsB. To address the above complications, the development of new sensing platforms for BR detection is necessary, which are efficient, sensitive, specific, affordable, easy-to-use, disposable, rapid, and amenable to automation and portability and also requiring small volumes of sample and reagents.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description and the drawings.

According to one or more exemplary embodiments, the present disclosure is directed to a method for measuring bilirubin concentration in a sample. An exemplary method may include preparing a sensing element, where the sensing element may include a plurality of carbon dots, adding the sample to the sensing element, where the sample may include a plurality of bilirubin molecules, obtaining a first grayscale image of the sensing element under ultra-violet (UV) irradiation, irradiating visible light with a wavelength between 470 nm and 490 nm on the sensing element, obtaining a second grayscale image of the sensing element under ultra-violet (UV) irradiation, calculating a light intensity difference by calculating a difference between a first average light intensity of the first grayscale image and a second average light intensity of the second image, and determining the bilirubin concentration based on a correlation between the bilirubin concentration and the light intensity difference.

According to one or more exemplary embodiments, the present disclosure is directed to a system for measuring bilirubin concentration in a sample. An exemplary system may include a testing chamber comprising a light-tight enclosure, a sensing element removably disposed within the testing chamber. An exemplary sensing element may include a bacterial cellulose nanopaper, and a plurality of carbon dots embedded within the bacterial cellulose nanopaper. An exemplary sample may be deposited on a top surface of the sensing element. An exemplary system may further include at least one UV light source that may be disposed within the testing chamber, where the at least one UV light source may be configured to irradiate UV light onto the top surface of the sensing element, at least one visible light source disposed within the testing chamber, where the at least one visible light source may be configured to irradiate visible light with a wavelength between 470 nm and 490 nm onto the top surface of the sensing element. An exemplary system may further include an image capturing device that may be disposed within the testing chamber, where the image capturing device may be configured to capture images or photos of the top surface of the sensing element.

An exemplary system may further include a processing unit that maybe coupled with the at least one UV light source, the at least one visible light source, and the image capturing device. An exemplary processing unit may include one or more processors, and a memory coupled with the one or more processors. An exemplary memory may be configured to store executable instructions to cause the one or more processors to irradiate the top surface of the sensing element with UV light by turning the at least one UV light source on, obtain a first image of the top surface of the sensing element utilizing the image capturing device, irradiate the top surface of the sensing element with visible light by turning the at least one visible light source on, obtain a second image of the top surface of the sensing element utilizing the image capturing device, convert the first image to a first grayscale image, convert the second image to a second grayscale image, calculate a first average light intensity of the first photo by averaging light intensities of a plurality of pixels of the first image, calculate a second average light intensity of the second image by averaging light intensities of a plurality of pixels of the second image, and calculating a light intensity difference by subtracting the first average light intensity from the second average light intensity.

In an exemplary embodiment, the memory may further store a correlation between the light intensity difference and the bilirubin concentration. An exemplary processor may further be configured to determine the bilirubin concentration based on the correlation between the bilirubin concentration and the light intensity difference.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
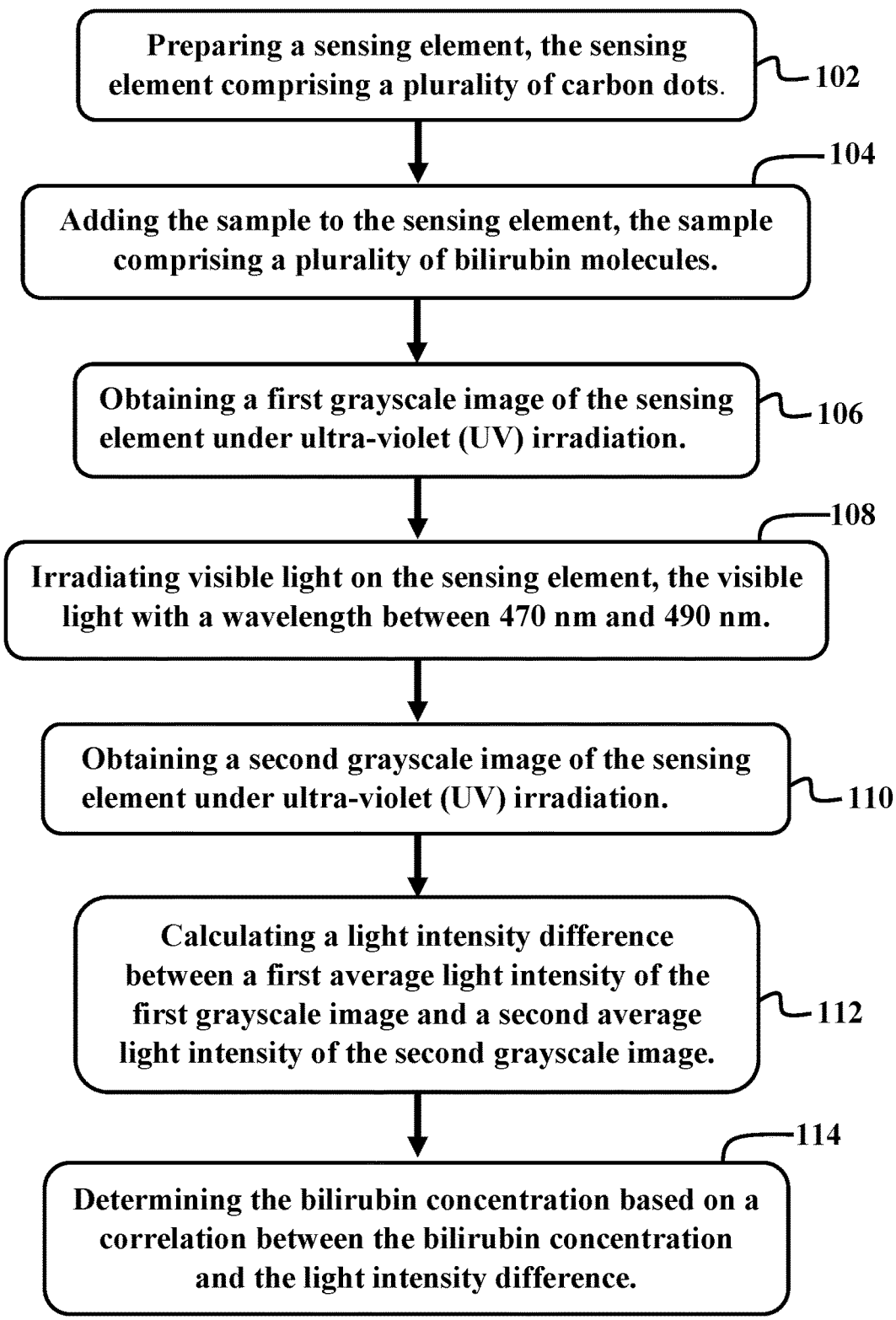
FIG. 1 illustrates a flowchart of a method for measuring bilirubin (BR) concentration in a sample, consistent with one or more exemplary embodiments of the present disclosure.

In the following detailed description, numerous specific details are set forth by way of examples to provide a thorough understanding of the relevant teachings related to the exemplary embodiments. However, it should be apparent that the present teachings may be practiced without such details. In other instances, well-known methods, procedures, components, and circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be plain to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Bacterial cellulose (BC) nanopaper-based (bio)sensing platforms, may be utilized in various (bio)sensing applications, including environmental monitoring, the detection of toxic materials, food quality control, and clinical/medical diagnostics. These wide ranges of application for BC nanopapers may be attributed to the fascinating and unique physicochemical characteristics of BC nanopapers. A BC nanopaper may include a continuous sheet or film of nano-sized cellulose fibers. A BC nanopaper may be produced via bottom-up synthetic routes from carbon sources, such as glucose by some specific nonpathogenic bacteria, such as *Gluconacetobacter xylinus*. Apart from having the advantageous properties of cellulosic papers, including low cost, flexibility, porous matrix, printability, biocompatibility, and biodegradability, BC nanopapers further possess optical transparency, low thermal expansion, low surface roughness, and high mechanical and chemical stability.

Conventional methods and devices for measurement and monitoring of analytes mostly rely on expensive, nonportable, and sophisticated devices that may only be used in laboratories by trained operators. Exemplary systems provide low cost, portable, and easy-to-use analytical devices, which require only a simple scanner, to overcome the abovementioned problems of the conventional analytical methods and devices.

According to one or more exemplary embodiments, the present disclosure is directed to exemplary systems and methods for sensitive, specific, rapid, and easy diagnosis of neonatal jaundice via visual determination of BR level in infants' blood samples. An exemplary system may include an easy-to-use, cost-effective, non-toxic, disposable, and portable assay kit, which may be coupled with a smartphone as a color signal reader. In an exemplary system, highly photoluminescent carbon dots may be embedded in an exemplary BC nanopaper to obtain a carbon dot-embedded BC nanopaper (CDBN). An exemplary CDBN may be used as a sensing element in an exemplary system for visual determination of BR level in infants' blood samples. Photoluminescence (PL) of an exemplary CDBN may be first be quenched upon addition of an exemplary sample containing BR. A grayscale image of the exemplary quenched CDBN may be obtained by an image capturing device such as an integrated smartphone camera. After that, PL of an exemplary quenched CDBN may be recovered by irradiating blue light onto the exemplary quenched CDBN for a predetermined period of time. A second grayscale image of an exemplary recovered CDBN may be obtained by an exemplary image capturing device. A light intensity difference between the first grayscale image and the second grayscale image may be obtained by determining a difference between average pixel light intensities of the first and the second grayscale images. An exemplary system may be calibrated such that a concentration of BR within an exemplary sample may be determined based on a correlation between the light intensity difference and BR concentration. An exemplary correlation between the light intensity difference and BR concentration may be a linear correlation obtained from calibration of an exemplary system.

According to one or more exemplary embodiments, the present disclosure may be directed to exemplary methods, exemplary apparatus, and exemplary systems for determining and presenting quantitative, visual measurements of BR levels in an exemplary blood sample utilizing a sensing platform, in which a BC nanopaper may be used as a sensing element. An exemplary BC nanopaper-based sensing element of an exemplary sensing platform may be embedded by carbon dots to form a photoluminescent sensing element. An accurate, consistent, and reliable quantitative measurement of BR level in an exemplary sample may be achieved by depositing an exemplary blood sample onto an exemplary photoluminescent sensing element. Deposition of an exemplary blood sample containing BR onto an exemplary photoluminescent sensing element may cause the exemplary photoluminescent sensing element to undergo a quenching process. In an exemplary quenching process photoluminescence of an exemplary photoluminescent sensing element may reduce due to the presence of BR. After that, photoluminescence of an exemplary quenched sensing element may be recovered by irradiating blue light onto the exemplary quenched sensing element. Under blue light irradiation, unconjugated BR molecules may undergo a photoisomerization and may be converted to colorless products. Photoisomerization of unconjugated BR molecules may lead to the recovery of photoluminescence of an exemplary quenched sensing element. Concentration of unconjugated BR within an exemplary blood sample may be determined by obtaining a light intensity difference between grayscale images taken from an exemplary sensing element before and after the recovery of photoluminescence of the exemplary sensing element. A linear correlation may exist between concentration of BR and the obtained light intensity difference. The linear correlation may be obtained by calibration.

An exemplary system and apparatus for measuring bilirubin concentration in a blood sample may further include a testing chamber. An exemplary testing chamber may provide an internal environment that may be light-tight such that essentially all light not used for imaging or recovering an exemplary sensing element may be excluded regardless of ambient conditions. In an exemplary system, an exemplary sensing element may be disposed within the testing chamber. An exemplary testing chamber may further enclose light sources including but not limited to at least one UV light source and at least one visible light source that may be configured to irradiate diffuse lights onto an exemplary sensing element. In exemplary embodiments, an exemplary testing chamber being light-tight with respect to the ambient and exemplary light sources being disposed within the exemplary light-tight testing chamber may insure a consistent optical and imaging environment for every sensing element, therefore rendering exemplary methods for measuring bilirubin concentration in a blood sample platform-independent.

FIG. 1 illustrates a flowchart of a method 100 for measuring bilirubin (BR) concentration in a sample, consistent with one or more exemplary embodiments of the present disclosure. In an exemplary embodiment, method 100 may include a step 102 of preparing a sensing element that may include a plurality of carbon dots, a step 104 of adding a sample including BR molecules to the sensing element, a step 106 of obtaining a first grayscale image of the sensing element under ultra-violet (UV) irradiation, a step 108 of irradiating visible light on the sensing element, where the visible light may have a wavelength between 470 nm and 490 nm, a step 110 of obtaining a second grayscale image of the sensing element under ultra-violet (UV) irradiation, a step 112 of calculating a light intensity difference by calculating a difference between a first average light intensity of the first grayscale image and a second average light intensity of the second image, and a step 114 of determining the BR concentration based on a correlation between the BR concentration and the light intensity difference.

In an exemplary embodiment, step 102 of preparing a sensing element that may include a plurality of carbon dots may include embedding the plurality of carbon dots within a BC nanopaper. In an exemplary embodiment, the plurality of photoluminescent carbon dots may be synthesized by a hydrothermal method. For example, 500 μL EDA may be added to 500 mg citric acid and the mixture may be diluted with 10 mL of water. The diluted mixture may then be transferred to a Teflon-lined stainless steel autoclave, where it may be heated for 5 hours at 200° C. In an exemplary embodiment, an obtained solution of carbon dots may have a dilution ratio between 0.02 and 1.00.

Figure 6A:
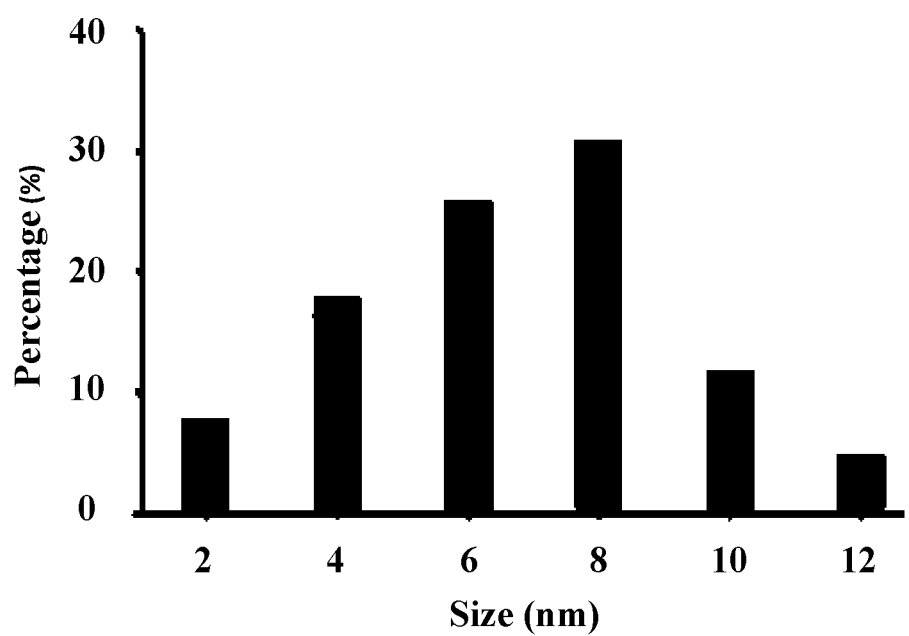
FIG. 6A illustrates a dynamic light scattering (DLS) analysis of synthesized carbon dots, consistent with one or more exemplary embodiments of the present disclosure.

FIG. 6A illustrates a dynamic light scattering (DLS) analysis of synthesized carbon dots, consistent with one or more exemplary embodiments of the present disclosure. In an exemplary embodiment, the plurality of carbon dots may have an average dimeter of 2 nm to 12 nm.

Figure 6B:
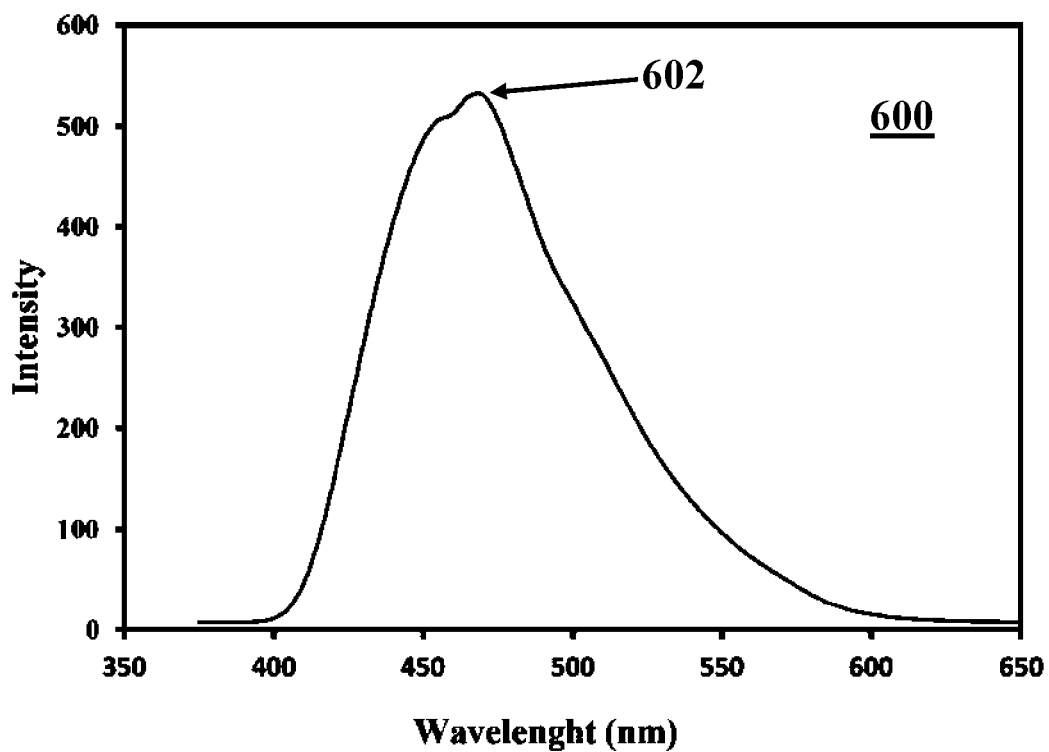
FIG. 6B illustrates photoluminescent spectrum of the synthesized carbon dots solution, consistent with one or more exemplary embodiments of the present disclosure.

FIG. 6B illustrates photoluminescent spectrum 600 of the synthesized carbon dots solution, consistent with one or more exemplary embodiments of the present disclosure. In an exemplary embodiment, the synthesized carbon dots solution exhibits a characteristic peak 602 at a wavelength of 465 nm, which may indicate the photoluminescence of the synthesized carbon dots.

In an exemplary embodiment, embedding the plurality of carbon dots within a BC nanopaper may include drop-casting a solution of carbon dots onto the BC nanopaper. In an exemplary embodiment, drop-casting the solution of carbon dots onto the BC nanopaper may include depositing the synthesized carbon dots solution onto a patterned BC nanopaper in a drop-wise manner and then drying the drop-casted solution at room temperature. In an exemplary embodiment, the patterned BC nanopaper may have a circular pattern. For example, a wet BC nanopaper sheet may be dewatered by placing the wet BC nanopaper between two normal filter papers. The wet BC nanopaper along with the two filter papers may be sandwiched between two glass plates, and then may be dried in an oven for 12 hours at 100° C. After that, the dried BC nanopaper may be patterned. For example, a suitable pattern for the dried BC nanopaper may be a circular pattern with a diameter of approximately 5 mm. After that, the synthesized carbon dots solution may be added to the patterned BC nanopaper in a drop-wise manner. The drop-casted carbon dot solution may be dried at room temperature for 30 minutes to obtain a CDBN sensing element.

Figure 6C:
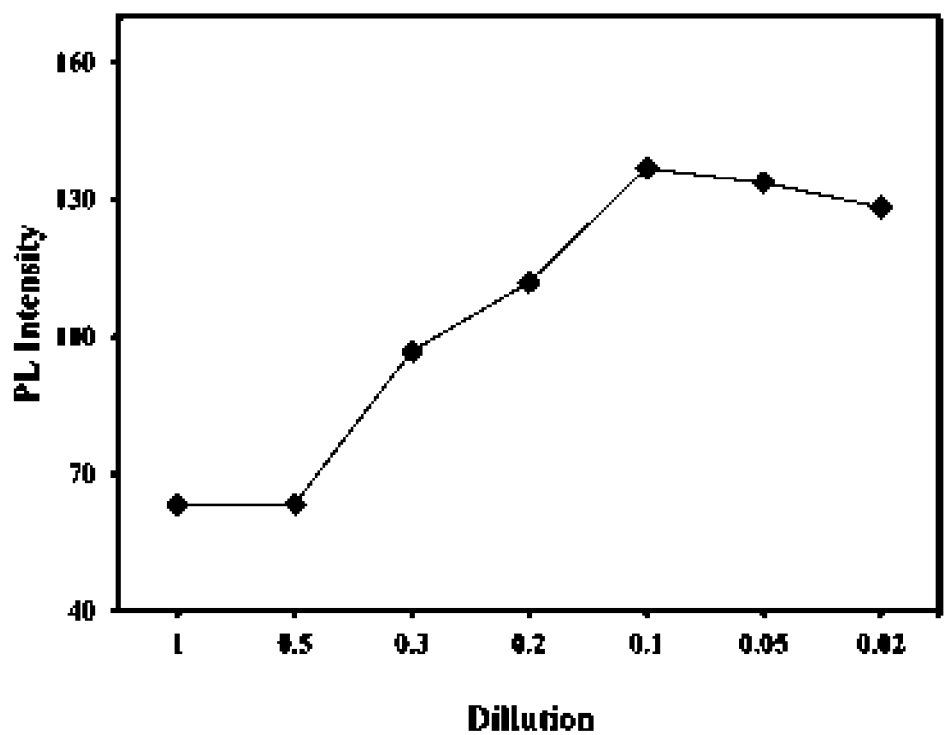
FIG. 6C illustrates a graph of photoluminescent intensity of a CDBN sensing element versus dilution amounts of carbon dots solution, consistent with one or more exemplary embodiments of the present disclosure.

FIG. 6C illustrates a graph of photoluminescent intensity of a CDBN sensing element versus dilution amounts of carbon dots solution, consistent with one or more exemplary embodiments of the present disclosure. In an exemplary embodiment, to assess the effect of the dilution ratio of the carbon dots solution, photoluminescent intensity of the fabricated CDBN sensing element was evaluated at various dilution ratios in the range of 0.02 to 1.00. As evident from the results presented in FIG. 6C, a maximum of photoluminescent intensity occurs at a dilution ratio of 0.1. Accordingly, in an exemplary embodiment, a carbon dots solution that may be added to a BC nanopaper to obtain a CDBN sensing element may have a dilution ratio between 0.02 and 1.00. In an exemplary embodiment, a carbon dots solution that may be added to a BC nanopaper to obtain a CDBN sensing element may have a dilution ratio of approximately 0.1.

In an exemplary embodiment, step 104 of adding a sample including BA molecules to the sensing element may include adding a human blood sample to the sensing element. As used herein, adding a human blood sample to the sensing element may refer to depositing a human blood sample onto the obtained CDBN sensing element in a drop-wise manner. In an exemplary embodiment, the human blood sample may include a blood sample obtained from neonates between the ages of 1 and 7 days. In an exemplary embodiment, the human blood sample may include a one drop blood specimen, the red blood cells of which may be separated by a plasma separation membrane.

In an exemplary embodiment, adding a sample containing BR molecules to the CDBN sensing element may quench or in other words reduce the photoluminescent emission of the CDBN sensing element. This photoluminescence quenching of the fabricated CDBN sensing element upon addition of a sample containing BR molecules may be attributed to the fluorescence resonance energy transfer and the inner filter effect of BR toward embedded carbon dots within the fabricated CDBN sensing element. This inner filter effect of BR toward embedded carbon dots may be originated from an overlap between UV-vis absorption spectrum of BR and photoluminescence emission of the synthesized carbon dots solution.

Figure 7:
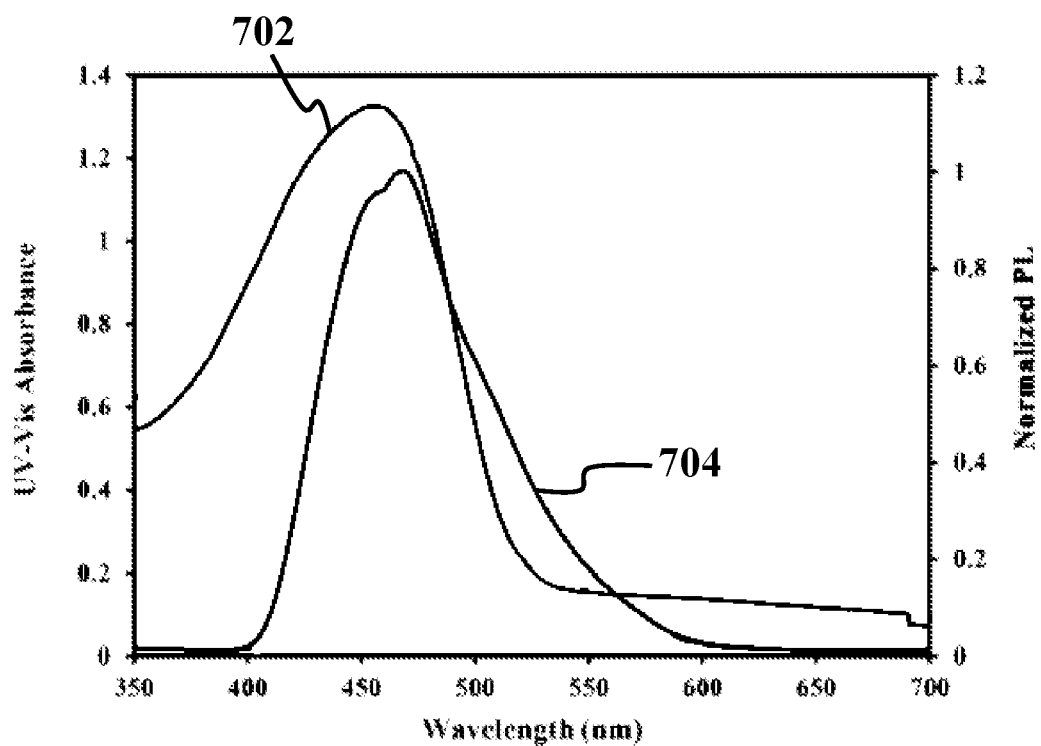
FIG. 7 illustrates UV-vis absorption spectrum of BR and normalized photoluminescence emission of synthesized carbon dots solution, consistent with one or more exemplary embodiments of the present disclosure.

FIG. 7 illustrates UV-vis absorption spectrum 702 of BR and normalized photoluminescence emission 704 of synthesized carbon dots solution, consistent with one or more exemplary embodiments of the present disclosure. Referring to FIG. 7, an overlap exists between UV-vis absorption spectrum 702 of BR and photoluminescence emission 704 of the synthesized carbon dots solution. This overlap, as discussed above, may lead to an inner filter effect of BR toward embedded carbon dots, which in turn may cause quenching of the photoluminescence of the fabricated CDBN sensing element.

In an exemplary embodiment, step 106 of obtaining a first grayscale image of the sensing element under ultra-violet (UV) irradiation may include irradiating UV light onto the sensing element, obtaining a first color image of the sensing element, and converting the first color image of the sensing element into the first grayscale image of the sensing element. In an exemplary embodiment, step 106 of obtaining a first grayscale image of the sensing element under ultra-violet (UV) irradiation may further include isolating the sensing element from ambient light by enclosing the sensing element within a light-tight enclosure. In an exemplary embodiment, a UV light source within the light-tight enclosure may be utilized for irradiating UV light onto the sensing element. In an exemplary embodiment, an image recording device, such as an integrated smartphone camera may be utilized for obtaining the first color image of the sensing element. An exemplary first color image of the sensing element may include a plurality of pixels and each pixel of the plurality of pixels may have an RGB color value. In an exemplary embodiment, the first color image of the sensing element may be converted into a first grayscale image of the sensing element. Each exemplary pixel of an exemplary first grayscale image of the sensing element may have only a light intensity value. A first average light intensity value for all the pixels within the first grayscale image of the sensing element may be obtained by averaging light intensities of the plurality of pixels within the first grayscale image of the sensing element.

In an exemplary embodiment, step 108 of irradiating visible light on the sensing element may include irradiating a visible light with a wavelength between 470 nm and 490 nm. As used herein, a visible light with a wavelength between 470 nm and 490 nm may be referred to as a blue light. In an exemplary embodiment, sensing strategy utilized in method 100 is based on recovering the quenched photoluminescence of the fabricated CDBN sensing element by blue light irradiation onto the fabricated CDBN sensing element for a predetermined amount of time. Under blue light radiation BR molecules may undergo photoisomerization and photooxidation that may lead to unconjugated BR molecules to be converted to colorless products without a quenching effect on photoluminescent emission of the fabricated CDBN. This photoisomerization and photo oxidation of BR molecules may lead to an increase in photoluminescent emission of the fabricated CDBN sensing element. In unconjugated BR structure, the bridging exocyclic double bond in each of the two dipyrrinones has a Z configuration as the most stable form. The unconjugated isomer is a water insoluble form of BR that is stabilized via intramolecular H-bonding. In the presence of blue light, the configurational isomerization occurs and lumirubins may be formed. Since BR is an oxygen-sensitive molecule, in the presence of dissolved oxygen in the samples, the photooxidation process may occur following the photoisomerization and subsequently the polar, colorless, and water-soluble oxidation products may be formed. Accordingly, in an exemplary embodiment, step 108 may involve recovering photoluminescent emission of the fabricated CDBN sensing element by irradiating a visible light with a wavelength between 470 nm and 490 nm for a predetermined amount of time. In an exemplary embodiment, the predetermined amount of time may be between 1 and 10 minutes.

In an exemplary embodiment, step 110 of obtaining a second grayscale image of the sensing element under ultra-violet (UV) irradiation may include irradiating UV light onto the sensing element, obtaining a second color image of the sensing element, and converting the second color image of the sensing element into the second grayscale image of the sensing element. In an exemplary embodiment, step 106 of obtaining a second grayscale image of the sensing element under ultra-violet (UV) irradiation may further include isolating the sensing element from ambient light by enclosing the sensing element within a light-tight enclosure. In an exemplary embodiment, a UV light source within the light-tight enclosure may be utilized for irradiating UV light onto the sensing element. In an exemplary embodiment, an image recording device, such as an integrated smartphone camera may be utilized for obtaining the second color image of the sensing element. An exemplary second color image of the sensing element may include a plurality of pixels and each pixel of the plurality of pixels may have an RGB color value. In an exemplary embodiment, the second color image of the sensing element may be converted into a second grayscale image of the sensing element. Each exemplary pixel of an exemplary second grayscale image of the sensing substrate may have only a light intensity value. A second average light intensity value for all the pixels within the second grayscale image of the sensing element may be obtained by averaging light intensities of the plurality of pixels within the second grayscale image of the sensing element.

In an exemplary embodiment, step 112 may include calculating a light intensity difference by calculating a difference between the first average light intensity of the first grayscale image and the second average light intensity of the second image. In an exemplary embodiment, obtaining the first average light intensity of the first grayscale image was described above in connection with step 106 and obtaining the second average light intensity of the second grayscale image was described above in connection with step 110. In an exemplary embodiment, the light intensity difference may be obtained by subtracting the first average light intensity from the second average light intensity. In other words, the light intensity difference may include a difference between an average light intensity of a grayscale image of a quenched CDBN sensing element and an average light intensity of a grayscale image of a recovered CDBN sensing element. Accordingly, since the major factor affecting the average light intensity between the two images is the concentration of the unconjugated BR molecules, a calibration curve may be obtained that may correlate the concentration of BR within the sample and the light intensity difference obtained in step 112.

In an exemplary embodiment, step 114 of determining the BR concentration based on a correlation between the BR concentration and the light intensity difference may involve finding a correlation between the BR concentration and the light intensity difference. In an exemplary embodiment, this correlation may be obtained by determining the light intensity difference in the presence of a plurality of samples with known amounts of BR. In an exemplary embodiment, in order to determine a correlation between BR concentration and the light intensity difference, different samples containing different concentrations of BR may be prepared. For example, 19 samples containing different BR concentrations ranging between 2-20 mg $dL^{-1}$ may be analyzed utilizing method 100 in order to obtain a light intensity difference for each sample. Then a calibration curve may be obtained that may be used for correlating the BR concentration within a sample and the light intensity difference obtained according to steps 102 to 112 of method 100.

Figure 8:
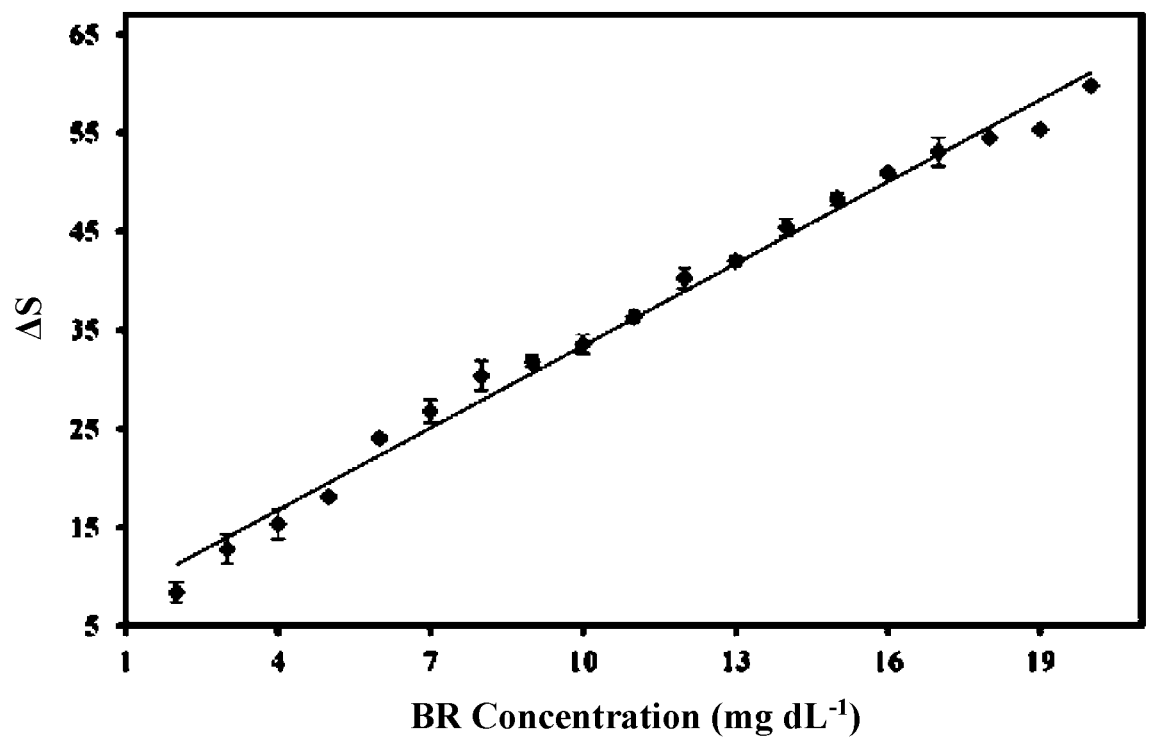
FIG. 8 illustrates an exemplary calibration curve obtained for a fabricated CDBN sensing element, consistent with one or more exemplary embodiments of the present disclosure.

FIG. 8 illustrates an exemplary calibration curve obtained for a fabricated CDBN sensing element, consistent with one or more exemplary embodiments of the present disclosure. In an exemplary embodiment, the calibration curve was linear in a range of 2-20 mg $dL^{-1}$ of BR with a correlation coefficient of 0.9950. The linear regression equation for BR concentration may be presented as Equation (1) below:

$$\Delta S=2.772C+5.664 \qquad \text{Equation (1)}$$

In Equation (1) above, $\Delta S$ denotes the light intensity difference and C denotes the bilirubin concentration in mg $dL^{-1}$. In an exemplary embodiment, step 114 of determining the BR concentration based on a correlation between the BR concentration and the light intensity difference may include determining the BR concentration based on a correlation defined by Equation (1).

Figure 2:
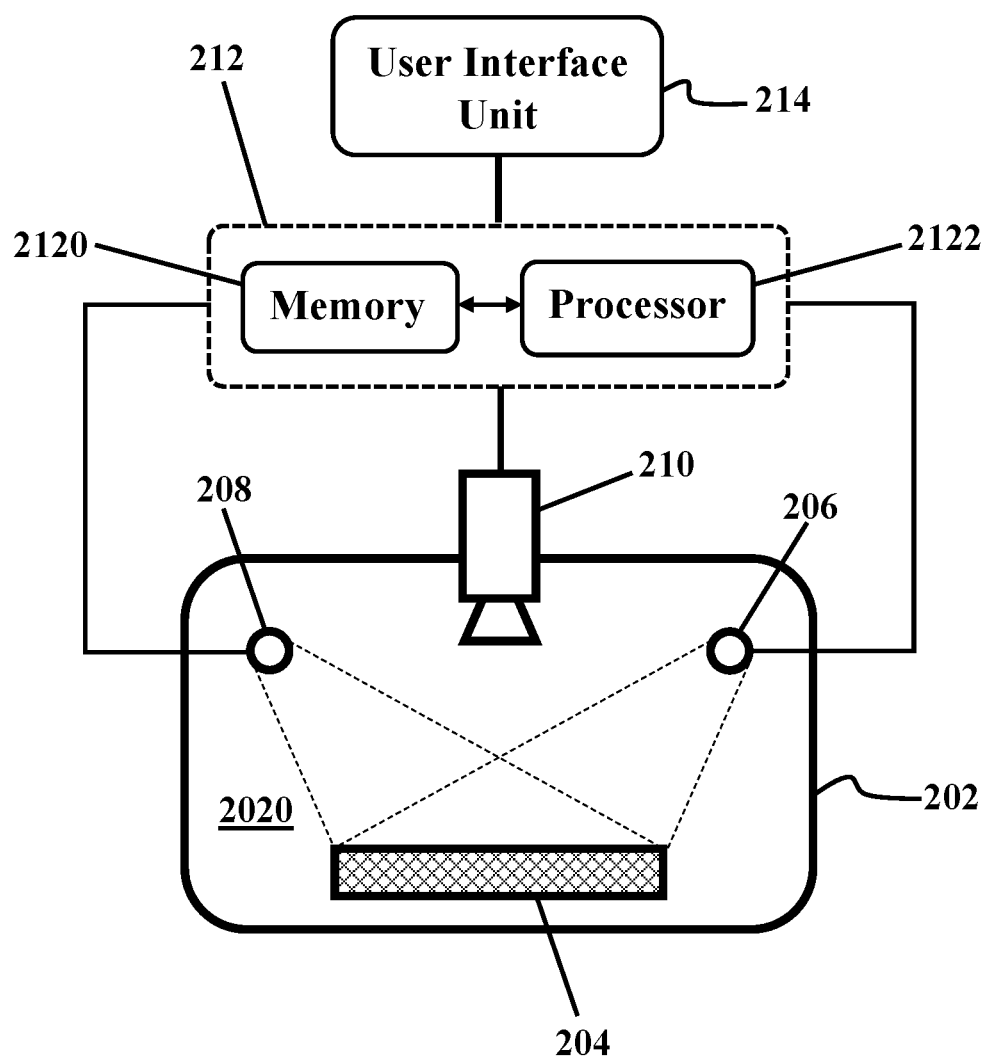
FIG. 2 illustrates a system for measuring BR concentration in a sample, consistent with one or more exemplary embodiments of the present disclosure. In an exemplary embodiment.

FIG. 2 illustrates a system 200 for measuring BR concentration in a sample, consistent with one or more exemplary embodiments of the present disclosure. In an exemplary embodiment, system 200 may be utilized for implementing method 100. In an exemplary embodiment, system 200 may include a testing chamber 202, a sensing element 204 that may be removably disposed within testing chamber 202, at least one UV light source 206 that may be disposed within testing chamber 202, at least one visible light source 208 that may be disposed within testing chamber 202, an image capturing device 210, a processing unit 212, and a user interface unit 214 coupled to processing unit 212.

In an exemplary embodiment, testing chamber 202 may provide an internal environment 2020 that may be light-tight such that essentially all light not used for imaging or recovering an exemplary sensing element may be excluded regardless of ambient conditions. In an exemplary embodiment, all light within internal environment 2020 of testing chamber 202 may be limited to UV light provided by at least one UV light source 206 and visible light provided by at least one visible light source 208. In an exemplary embodiment, at least one UV light source 206 and at least one visible light source 208 may selectively be turned on and off. In an exemplary embodiment, turning at least one UV light source 206 and at least one visible light source 208 on and off may be carried out either manually or automatically by coupling at least one UV light source 206 and at least one visible light source 208 to processing unit 212. In an exemplary embodiment, processing unit 212 may be configured to implement method 100. Accordingly, processing unit 212 may be configured to selectively turn at least one UV light source 206 and at least one visible light source 208 on and off.

In an exemplary embodiment, at least one visible light source 208 may be a visible light LED capable of irradiating visible light with a wavelength between 470 nm and 490 nm. In an exemplary embodiment, at least one visible light source 208 may be a blue light LED that may be capable of irradiating a blue light with a wavelength of 470 nm.

Changes in light intensity while implementing method 100 utilizing system 200 may significantly change the light intensity measurements made with image capturing device 210. In exemplary embodiments, the best way to maintain light uniformity while capturing images of sensing element 204 utilizing image capturing device 210 may be to incorporate light sources (206, 208) within internal environment 2020 of testing chamber 202, as was described above in connection with FIG. 2.

In an exemplary embodiment, processing unit 212 may be coupled to image capturing device 210, at least one UV light source 206, at least one visible light source 208, and user interface unit 214 through, for example, wired links, wireless links, or a combination of wired and wireless links. In an exemplary embodiment, processing unit 212 may be configured to process obtained images of sensing element 204 before and after the recovery of photoluminescence of sensing element 204 to determine the BR concentration within a sample deposited on sensing element 204. In an exemplary embodiment, processing unit 212 may be further configured to control at least one UV light source 206, at least one visible light source 208, and image capturing device 210 for purposes that may include, for example, turning at least one UV light source 206 and at least one visible light source 208 on or off, or capturing images of sensing element 204.

In an exemplary embodiment, processing unit 212 may include a memory 2120 and a processor 2122. Memory 2120 may include executable instructions that, when executed, cause processor 2120 to perform operations to implement method 100. Such operations may include, for example, processing the received images from image capturing device 210 to determine the BR concentration in an exemplary sample deposited on sensing element 204. In an exemplary embodiment, operations may include receiving a first color image of sensing element 204 from image capturing device 210, converting the first color image to a first grayscale image, and calculating a first average light intensity of the first grayscale image. In an exemplary embodiment, operations may further include receiving a second color image of sensing element 204 from image capturing device 210, converting the second color image to a second grayscale image, calculating a second average light intensity of the second grayscale image. In an exemplary embodiment, operations may further include calculating a light intensity difference by subtracting the first average light intensity from the second average light intensity. In an exemplary embodiment, memory 2120 may further include a correlation between the light intensity difference obtained for a sample and BR concentration within that sample. In an exemplary embodiment, operations may further include determining the BR concentration based on the correlation between the BR concentration and the light intensity difference.

In an exemplary embodiment, user interface unit 214 may be configured to display the BR concentration measurement results. In an exemplary embodiment, user interface unit 214 may include a graphical user interface unit (GUI) that may be optionally configured to receive data input from a user. Data input by the user may include, for example, commands regarding turning at least one UV light source 206 and at least one visible light source 208 on or off, or capturing images of sensing element 204.

In an exemplary embodiment, processing unit 212 may be an integrated processing unit of a smartphone, user interface unit 214 may be a GUI of a software app installed on the smartphone, and image capturing device 210 may be an integrated camera of the smartphone. In an exemplary embodiment, at least one visible light source 208 may be an integrated light source of the smartphone. In an exemplary embodiment, upon loading the software app by a user, the app loads the calibration data and the GUI. After that, the user may deposit a blood sample onto sensing element 204. After depositing the blood sample, the user may insert sensing element 204 into testing chamber 202. The user may then execute the measurement instructions stored in the memory of the smartphone. Upon execution of measurement instructions, processing unit 212 may turn at least one UV light source 206 on and may urge image capturing device 210 to take the first color image of sensing element 204. After that, processing unit 212 may turn at least one visible light source 208 for a predetermined amount of time between 1 and 10 minutes. After that, processing unit 212 may urge image capturing device 210 to take the second color image of sensing element 204. The processing unit 212 may then determine the quantitative BR concentration based on a light intensity difference between grayscale versions of the first color image and the second color image and the loaded calibration data. Finally, the determined BR concentration may be displayed on the GUI.

Figure 3:
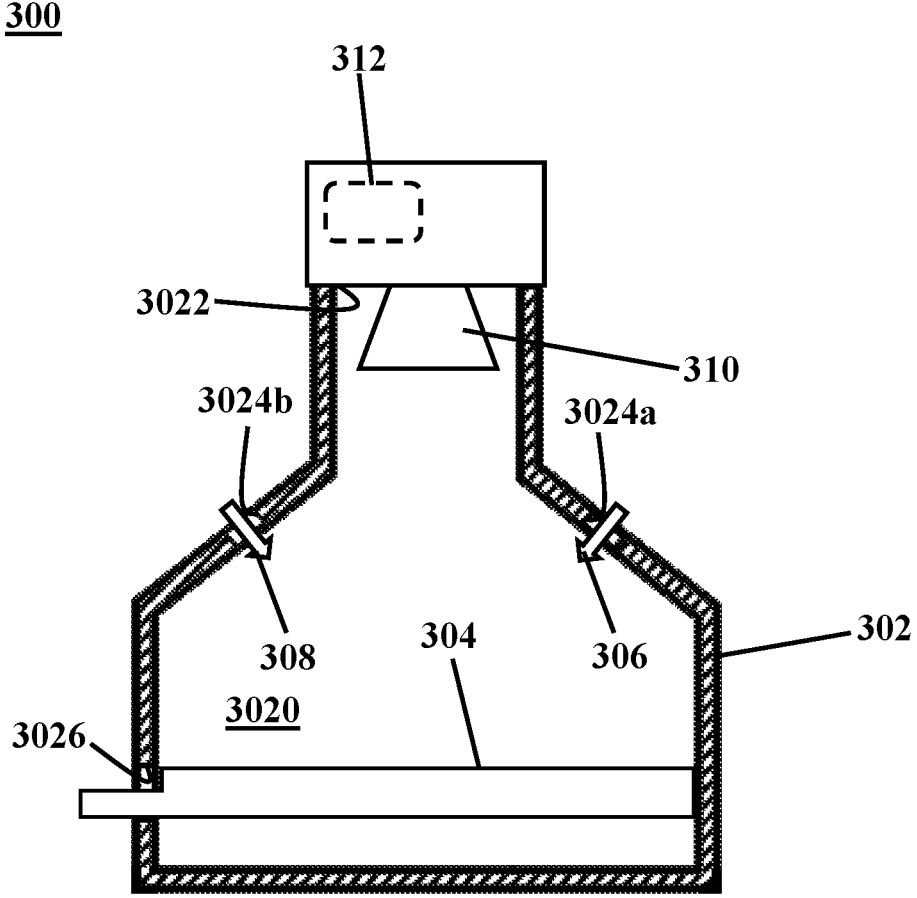
FIG. 3 illustrates an apparatus for measuring BR concentration in a sample, consistent with one or more exemplary embodiments of the present disclosure.

FIG. 3 illustrates an apparatus 300 for measuring BR concentration in a sample, consistent with one or more exemplary embodiments of the present disclosure. In an exemplary embodiment, apparatus 300 may be functionally similar to system 200. In an exemplary embodiment, apparatus 300 may be utilized for implementing steps of method 100.

In an exemplary embodiment, apparatus 300 may include a testing chamber 302, a sensing element 304 that may be removably disposed within testing chamber 302, at least one UV light source 306 that may be disposed within testing chamber 302, at least one visible light source 308 that may be disposed within testing chamber 302, an image capturing device 310, and a processing unit 312 similar to processing unit 212. In an exemplary embodiment, all elements of apparatus 300 may not be necessary for implementing steps of method 100.

In an exemplary embodiment, testing chamber 302 may be similar to testing chamber 202. In an exemplary embodiment, testing chamber 302 may provide an internal environment 3020 that may be light-tight such that essentially all light not used for imaging or recovering an exemplary sensing element may be excluded regardless of ambient conditions. In an exemplary embodiment, all light within internal environment 3020 of testing chamber 302 may be limited to UV light provided by at least one UV light source 306 and visible light provided by at least one visible light source 308.

In an exemplary embodiment, testing chamber 302 may include a top opening 3022 that may allow for image capturing device 312 to be fitted on top opening 3022 such that ambient light may not enter internal environment 3020 of testing chamber 302 from top opening 3022. In an exemplary embodiment, image capturing device 310 may be fitted on top opening 3022 such that image capturing device 310 may have a full view of a top surface of sensing element 304.

In an exemplary embodiment, testing chamber 302 may further include a plurality of lateral openings, such as lateral openings 3024a-b that may allow for mounting at least one UV light source 306 and at least one visible light source 308. In an exemplary embodiment, at least one UV light source 306 and at least one visible light source 308 may be mounted within lateral openings 3024a-b in a light-tight manner such that ambient light may not enter internal environment 3020 of testing chamber 302 from lateral openings 3024a-b.

In an exemplary embodiment, testing chamber 302 may further include a lateral slit 3026 that may allow for insertion of sensing element 304. In an exemplary embodiment, sensing element 304 may be inserted through lateral slit 3026 in a light-tight manner such that ambient light may not enter internal environment 3020 of testing chamber 302 from lateral slit 3026.

In an exemplary embodiment, apparatus 300 may be configured to implement method 100. For example, after performing step 102 of preparing a sensing element such as sensing element 304 that may include a plurality of carbon dots and step 104 of adding a sample including BR molecules to sensing element 304, sensing element 304 may be inserted into testing chamber 302 through lateral slit 3026. After that, method 100 may proceed to step 106 of obtaining a first grayscale image of the sensing element under ultra-violet (UV) irradiation. To this end, processing unit 312 may turn on at least one UV light source 306 and may urge image capturing device 310 to take a first color image of sensing element 304. The first color image of sensing element 304 may then be converted to a first grayscale image of sensing element 304 by processing unit 312. After that, method 100 may proceed to step 108 of irradiating visible light with a wavelength between 470 nm and 490 nm on sensing element 304. To this end, processing unit 312 may turn on at least one visible light source 308 for a predetermined time between 1 and 10 minutes. Then, in step 110 of obtaining a second grayscale image of the sensing element under ultra-violet (UV) irradiation, processing unit 312 may turn on at least one UV light source 306 and may urge image capturing device 310 to take a second color image of sensing element 304. The second color image of sensing element 304 may then be converted to a second grayscale image of sensing element 304 by processing unit 312. In an exemplary embodiment, processing unit 312 may be configured to calculate a light intensity difference between a first average light intensity of the first grayscale image and a second average light intensity of the second grayscale image and then determine the bilirubin concentration based on a correlation between the bilirubin concentration and the light intensity difference, as was discussed in connection with control unit 212 of system 200.

Figure 4:
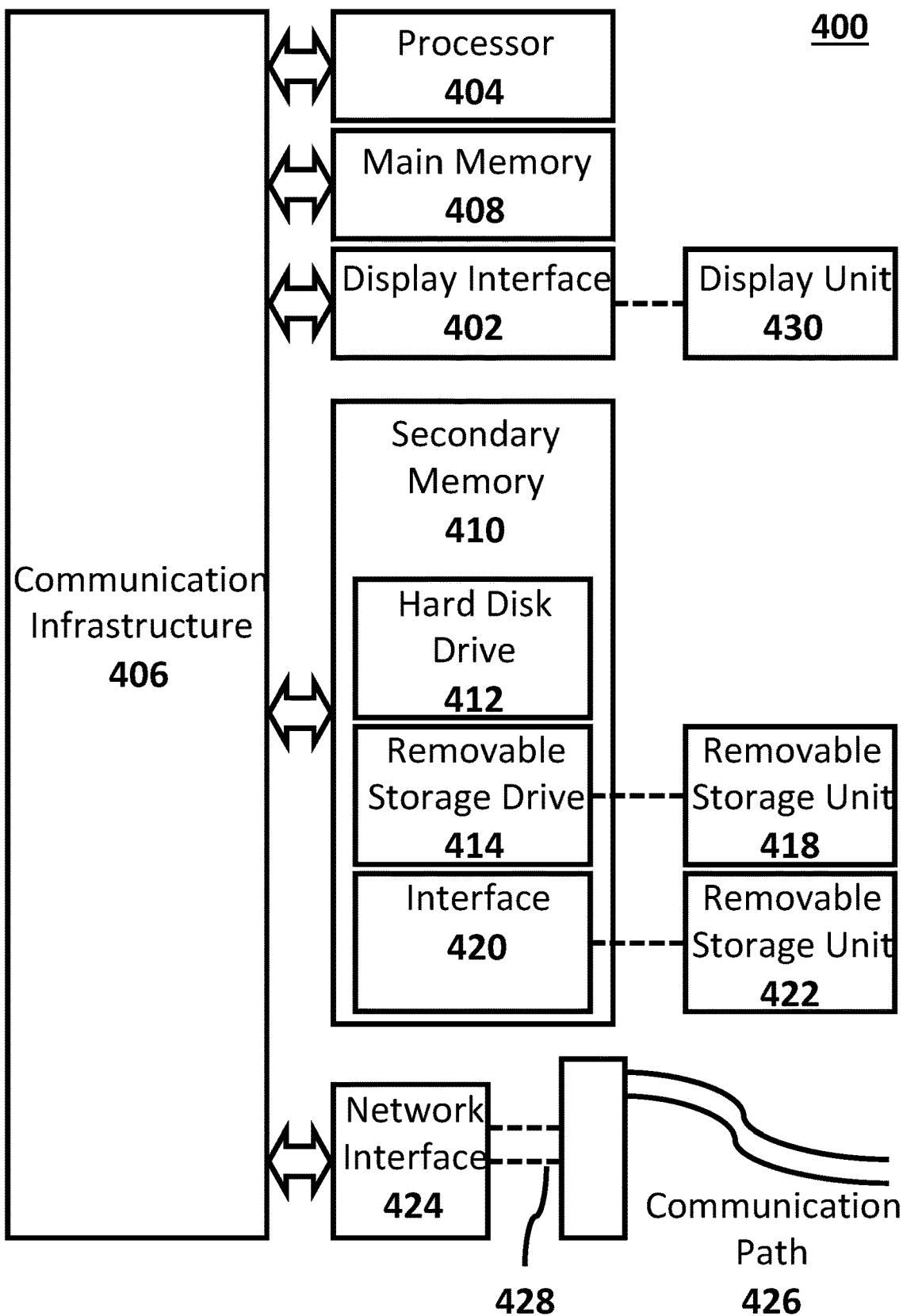
FIG. 4 shows a high-level functional block diagram of a processing unit, consistent with one or more exemplary embodiments of the present disclosure.

FIG. 4 shows a high-level functional block diagram of a processing unit 400, consistent with one or more exemplary embodiments of the present disclosure. For example, method 100 may be implemented in processing unit 400 using hardware, software, firmware, tangible computer readable media having instructions stored thereon, or a combination thereof and may be implemented in one or more processing units or other processing systems.

If programmable logic is used, such logic may execute on a commercially available processing platform or a special purpose device. One ordinary skill in the art may appreciate that an embodiment of the disclosed subject matter can be practiced with various processing unit configurations, including multi-core multiprocessor systems, minicomputers, mainframe computers, computers linked or clustered with distributed functions, as well as pervasive or miniature computers that may be embedded into virtually any device.

For instance, a processing unit having at least one processor device and a memory may be used to implement the above-described embodiments. A processor device may be a single processor, a plurality of processors, or combinations thereof. Processor devices may have one or more processor "cores."

An embodiment of the invention is described in terms of this example processing unit 500. After reading this description, it will become apparent to a person skilled in the relevant art how to implement the invention using other processing units and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 404 may be a special purpose or a general-purpose processor device. As will be appreciated by persons skilled in the relevant art, processor device 404 may also be a single processor in a multi-core/multiprocessor system, such system operating alone, or in a cluster of processing units operating in a cluster or server farm. Processor device 404 may be connected to a communication infrastructure 406, for example, a bus, message queue, network, or multi-core message-passing scheme.

In an exemplary embodiment, processing unit 400 may include a display interface 402, for example a video connector, to transfer data to a display unit 430, for example, a monitor. Processing unit 400 may also include a main memory 408, for example, random access memory (RAM), and may also include a secondary memory 410. Secondary memory 410 may include, for example, a hard disk drive 412, and a removable storage drive 414. Removable storage drive 414 may include a floppy disk drive, a magnetic tape drive, an optical disk drive, a flash memory, or the like. Removable storage drive 414 may read from and/or write to a removable storage unit 418 in a well-known manner. Removable storage unit 418 may include a floppy disk, a magnetic tape, an optical disk, etc., which may be read by and written to by removable storage drive 414. As will be appreciated by persons skilled in the relevant art, removable storage unit 418 may include a computer usable storage medium having stored therein computer software and/or data.

In alternative implementations, secondary memory 410 may include other similar means for allowing computer programs or other instructions to be loaded into processing unit 400. Such means may include, for example, a removable storage unit 422 and an interface 420. Examples of such means may include a program cartridge and cartridge interface (such as that found in video game devices), a removable memory chip (such as an EPROM, or PROM) and associated socket, and other removable storage units 422 and interfaces 420 which allow software and data to be transferred from removable storage unit 422 to processing unit 400.

Processing unit 400 may also include a communications interface 424. Communications interface 424 allows software and data to be transferred between processing unit 400 and external devices. Communications interface 424 may include a modem, a network interface (such as an Ethernet card), a communications port, a PCMCIA slot and card, or the like. Software and data transferred via communications interface 424 may be in the form of signals, which may be electronic, electromagnetic, optical, or other signals capable of being received by communications interface 424. These signals may be provided to communications interface 424 via a communications path 426. Communications path 426 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 418, removable storage unit 422, and a hard disk installed in hard disk drive 412. Computer program medium and computer usable medium may also refer to memories, such as main memory 408 and secondary memory 410, which may be memory semiconductors (e.g. DRAMs, etc.).

Computer programs (also called computer control logic) are stored in main memory 408 and/or secondary memory 410. Computer programs may also be received via communications interface 424. Such computer programs, when executed, enable processing unit 400 to implement different embodiments of the present disclosure as discussed herein. In particular, the computer programs, when executed, enable processor device 404 to implement the processes of the present disclosure, such as the operations in method 100 illustrated by flowchart 100 of FIG. 1. Accordingly, such computer programs represent controllers of processing unit 400. Where an exemplary embodiment of method 100 is implemented using software, the software may be stored in a computer program product and loaded into processing unit 400 using removable storage drive 414, interface 420, and hard disk drive 412, or communications interface 424. In an exemplary embodiment, processing unit 400 may represent analogous elements in FIGS. 2 and 3.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random-access memory), secondary storage devices (e.g., hard drives, floppy disks, CD ROMS, ZIP disks, tapes, magnetic storage devices, and optical storage devices, MEMS, nano-technological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

Figure 5A:
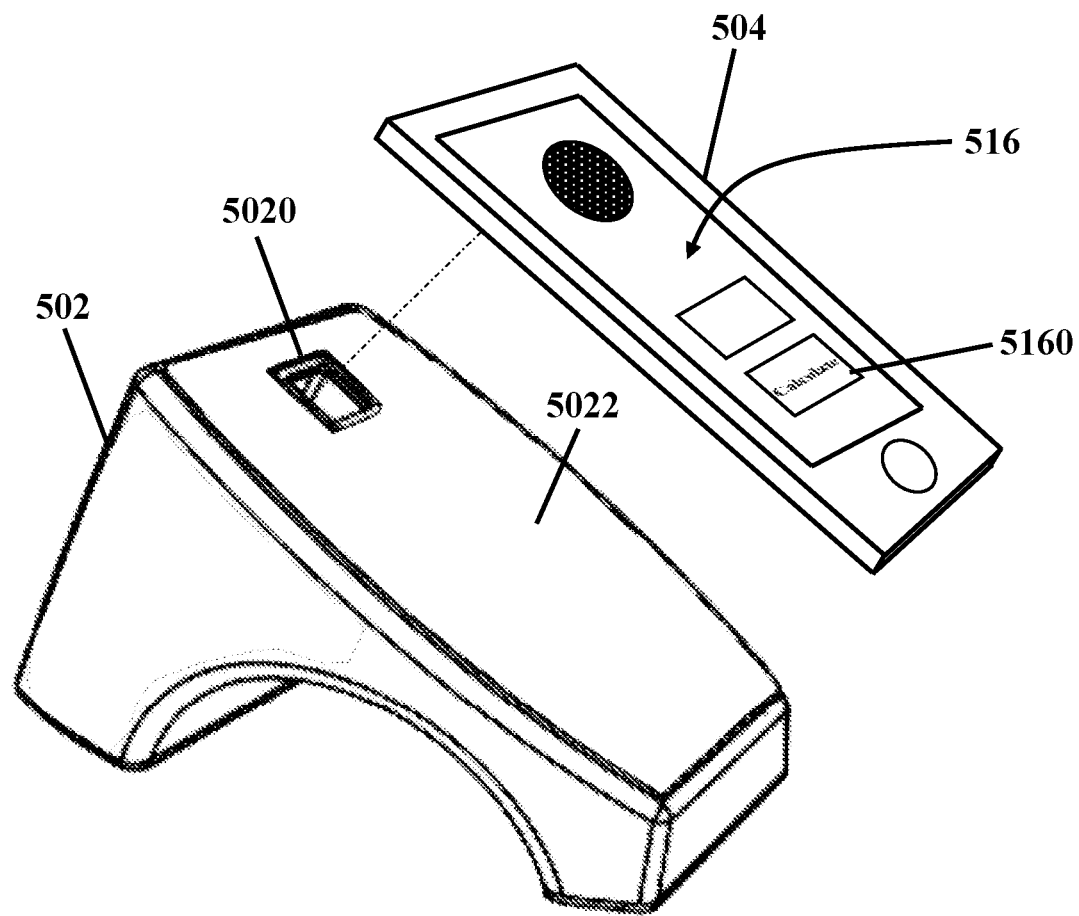
FIG. 5A illustrates a perspective view of a smartphone-based apparatus for measuring BA concentration in a sample, consistent with one or more exemplary embodiments of the present disclosure.
Figure 5B:
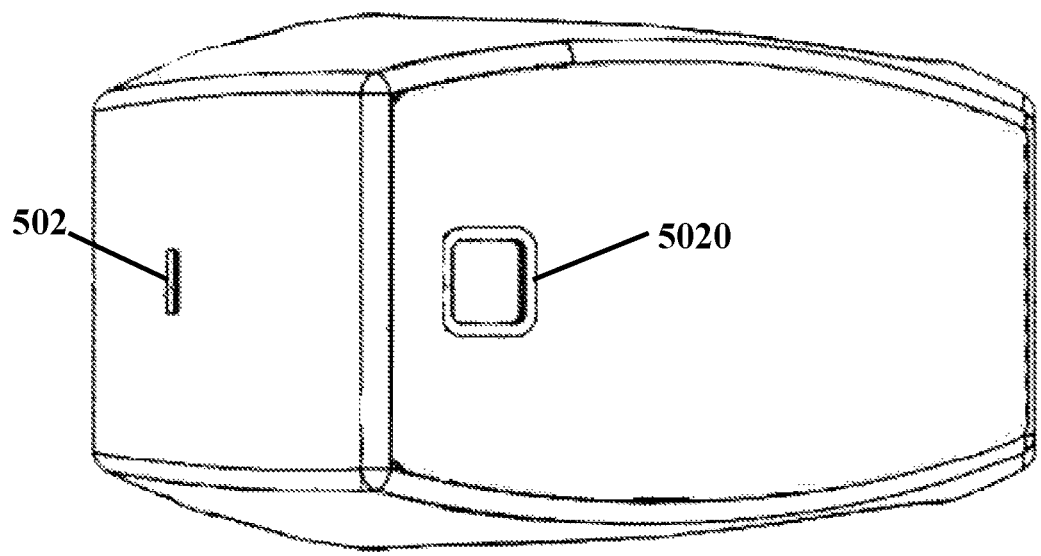
FIG. 5B illustrates a top view of a smartphone-based apparatus for measuring BA concentration in a sample, consistent with one or more exemplary embodiments of the present disclosure.
Figure 5C:
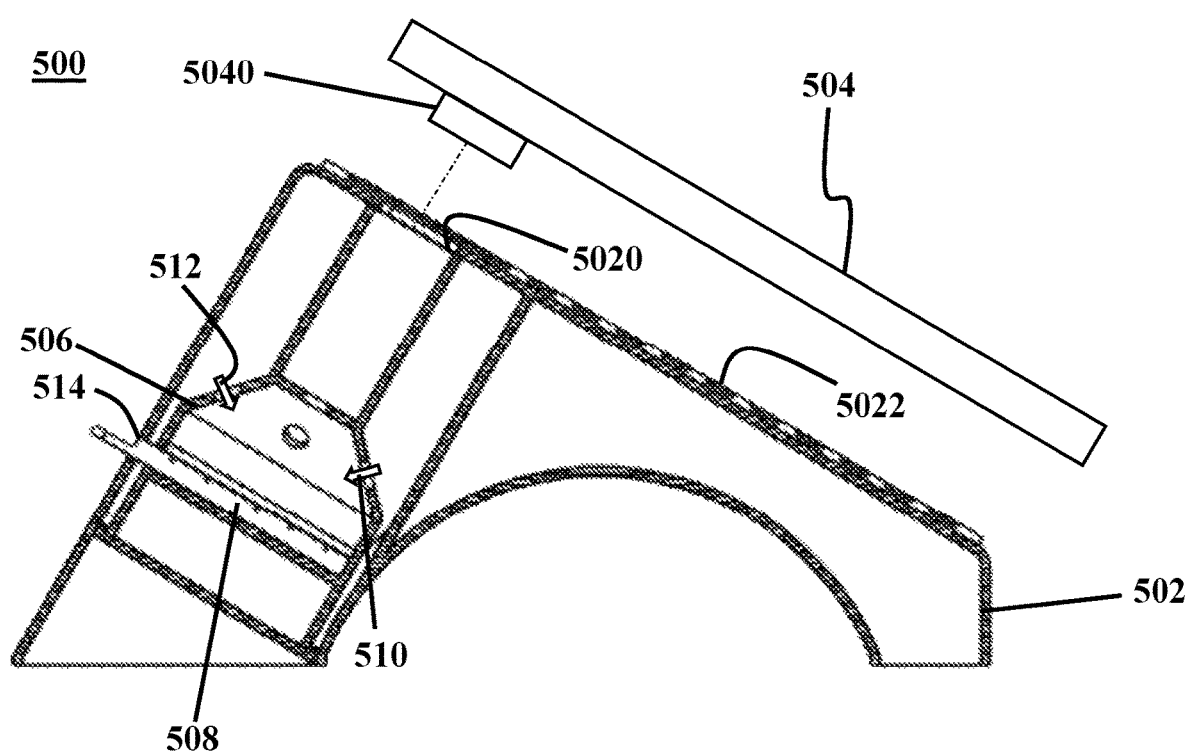
FIG. 5C illustrates a sectional side view of a smartphone-based apparatus for measuring BA concentration in a sample, consistent with one or more exemplary embodiments of the present disclosure.

FIG. 5A illustrates a perspective view of a smartphone-based apparatus 500 for measuring BA concentration in a sample, consistent with one or more exemplary embodiments of the present disclosure. FIG. 5B illustrates a top view of a smartphone-based apparatus 500 for measuring BA concentration in a sample, consistent with one or more exemplary embodiments of the present disclosure. FIG. 5C illustrates a sectional side view of a smartphone-based apparatus 500 for measuring BA concentration in a sample, consistent with one or more exemplary embodiments of the present disclosure.

In an exemplary embodiment, smartphone-based apparatus 500 may include a main body 502 and a smartphone 504. In an exemplary embodiment, main body may include a top aperture 5020. Smartphone 504 may be detachably placed on a top surface 5022 of main body 502 such that an integrated camera 5040 of smartphone 504 may be fitted on top of aperture 5020.

In an exemplary embodiment, smartphone-based apparatus 500 may further include a testing chamber 506 similar to testing chamber 302, a sensing element 508 similar to sensing element 304 that may be removably disposed within testing chamber 506, at least one UV light source 510 similar to at least one UV light source 306 that may be disposed within testing chamber 506, and at least one visible light source 512 similar to at least one visible light source 308 that may be disposed within testing chamber 506. In an exemplary embodiment, main body 502 may further include a slit 514 similar to lateral slit 3026 that may allow for insertion of sensing element 508.

In an exemplary embodiment, smartphone-based apparatus 500 may be configured to implement steps of method 100. In an exemplary embodiment, additional apparatuses with similar functionality as apparatus 500 may be utilized to implement steps of method 100. For example, after performing step 102 of preparing a sensing element such as sensing element 508 that may include a plurality of carbon dots and step 104 of adding a sample including BR molecules to sensing element 508. Sensing element 508 may be inserted into testing chamber 506 through slit 514. After that, method 100 may proceed to step 106 of obtaining a first grayscale image of the sensing element under ultra-violet (UV) irradiation. To this end, integrated processing unit of smartphone 504 may turn on at least one UV light source 510 and may urge integrated camera 5040 to take a first color image of sensing element 508. The first color image of sensing element 508 may then be converted to a first grayscale image of sensing element 508 by the processing unit of smartphone 504. After that, method 100 may proceed to step 108 of irradiating visible light with a wavelength between 470 nm and 490 nm on sensing element 508. To this end, the processing unit of smartphone 504 may turn on at least one visible light source 308 for a predetermined time between 1 and 10 minutes. Then, in step 110 of obtaining a second grayscale image of the sensing element under ultra-violet (UV) irradiation, the processing unit of smartphone 504 may turn on at least one UV light source 510 and may urge integrated camera 5040 to take a second color image of sensing element 508. The second color image of sensing element 508 may then be converted to a second grayscale image of sensing element 508 by the processing unit of smartphone 504. In an exemplary embodiment, the processing unit of smartphone 504 may be configured to calculate a light intensity difference between a first average light intensity of the first grayscale image and a second average light intensity of the second grayscale image and then determine the bilirubin concentration based on a correlation between the bilirubin concentration and the light intensity difference.

In an exemplary embodiment, smartphone-based apparatus 500 may further include a user interface unit 516 that may be similar to user interface unit 214. In an exemplary embodiment, user interface unit 516 may be a GUI of a software app installed on the smartphone. User interface unit 516 may be configured to display the measured BR concentration. In an exemplary embodiment, user interface unit 516 may optionally be configured to receive data input from a user. Data input by the user may include, for example, commands regarding starting the measurement process by, for example, touching a command button 5160. For example, upon touching command button 5160 that may, for example, be a "calculate" button, the integrated processing unit of smartphone 504 may perform operations to further methods of measuring the concentration of BR, as was described in connection with processing unit 212 of FIG. 2.

The exemplary systems and methods for determining a concentration of BR within a blood sample may allow for determining BR concentration without any interference from other blood constituents. Biochemicals that may be present in a blood sample may include glucose, protein, albumin, uric acid, creatinine, urea, cyanocobalamin, L-ascorbic acid, L-phenylalanine, $Na^+$, $K^+$, $Mg^+$, $Ca^{2+}$, $Zn^{2+}$, $Cl^-$, and $HCO_3^-$. Many of the abovementioned biochemicals present in the blood sample may affect the luminescent emissions of an exemplary CDBNs. However, in the exemplary systems and methods, only BR responds to visible blue light irradiation. Hence, the analytical response of the exemplary CDBNs may not be affected by the presence of the aforementioned biochemicals.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications, and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A system for measuring bilirubin concentration in a sample, the system comprising:
   a testing chamber comprising a light-tight enclosure;
   a sensing element removably disposed within the testing chamber, the sensing element comprising:
      a bacterial cellulose nanopaper; and
      a plurality of carbon dots embedded within the bacterial cellulose nanopaper,
      wherein a top surface of the sensing element is configured to hold a deposit of the sample;
   at least one UV light source disposed within the testing chamber, the at least one UV light source configured to irradiate UV light onto the top surface of the sensing element;
   at least one visible light source disposed within the testing chamber, the at least one visible light source configured to irradiate visible light with a wavelength between 470 nm and 490 nm onto the top surface of the sensing element;
   an image capturing device disposed within the testing chamber, the image capturing device configured to capture images of the top surface of the sensing element; and
   a processing unit coupled with the at least one UV light source, the at least one visible light source, and the image capturing device, the processing unit comprising:
      one or more processors; and
      a non-transitory computer readable medium coupled with the one or more processors, the non-transitory computer readable medium configured to store executable instructions to cause the one or more processors to:
         irradiate the top surface of the sensing element with UV light by turning the at least one UV light source on;

obtain a first image of the top surface of the sensing element utilizing the image capturing device;
irradiate the top surface of the sensing element with visible light by turning the at least one visible light source on for a duration between 1 and 10 minutes;
obtain a second image of the top surface of the sensing element utilizing the image capturing device;
convert the first image to a first grayscale image;
convert the second image to a second grayscale image;
calculate a first average light intensity of the first image by averaging light intensities of a plurality of pixels of the first image;
calculate a second average light intensity of the second image by averaging light intensities of a plurality of pixels of the second image;
calculate a light intensity difference by subtracting the first average light intensity from the second average light intensity; and
wherein the non-transitory computer readable medium further stores a correlation between the light intensity difference and the bilirubin concentration, the processor further configured to determine the bilirubin concentration based on the correlation between the bilirubin concentration and the light intensity difference.

2. The system according to claim 1, wherein the correlation between the bilirubin concentration and the light intensity difference defined by:

$$\Delta S = 2.772C + 5.664,$$

wherein $\Delta S$ denotes the light intensity difference, and wherein C denotes the bilirubin concentration in mg $dL^{-1}$.

* * * * *